United States Patent
Ha et al.

(10) Patent No.: US 10,493,009 B2
(45) Date of Patent: Dec. 3, 2019

(54) STABLE PERSONAL CARE COMPOSITIONS CONTAINING A RETINOID

(71) Applicant: The Procter & Gamble Company, Cincinnati, OH (US)

(72) Inventors: Robert Bao Kim Ha, Liberty Township, OH (US); Joseph Harry Jansen, Harrison, OH (US); Mridula Manohar, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/840,874

(22) Filed: Dec. 13, 2017

(65) Prior Publication Data
US 2018/0161259 A1 Jun. 14, 2018

Related U.S. Application Data

(60) Provisional application No. 62/433,422, filed on Dec. 13, 2016.

(51) Int. Cl.
| | | |
|---|---|---|
| *A61K 8/37* | (2006.01) | |
| *A61K 8/91* | (2006.01) | |
| *A61K 8/891* | (2006.01) | |
| *A61Q 19/00* | (2006.01) | |
| *A61K 8/67* | (2006.01) | |
| *A61K 8/60* | (2006.01) | |
| *A61K 8/58* | (2006.01) | |
| *A61K 8/34* | (2006.01) | |
| *A61Q 17/04* | (2006.01) | |
| *A61K 8/81* | (2006.01) | |
| *A61K 8/06* | (2006.01) | |

(52) U.S. Cl.
CPC .............. *A61K 8/37* (2013.01); *A61K 8/062* (2013.01); *A61K 8/342* (2013.01); *A61K 8/375* (2013.01); *A61K 8/585* (2013.01); *A61K 8/602* (2013.01); *A61K 8/671* (2013.01); *A61K 8/8152* (2013.01); *A61K 8/891* (2013.01); *A61K 8/91* (2013.01); *A61Q 17/04* (2013.01); *A61Q 19/00* (2013.01); *A61K 2800/412* (2013.01); *A61K 2800/52* (2013.01)

(58) Field of Classification Search
CPC . A61K 8/37; A61K 8/375; A61K 8/91; A61K 8/891; A61K 8/671; A61K 8/602; A61K 8/585; A61K 8/342; A61K 8/062; A61K 8/8152; A61K 2800/412; A61K 2800/52; A61Q 19/00; A61Q 17/04
See application file for complete search history.

(56) References Cited

U.S. PATENT DOCUMENTS

| | | |
|---|---|---|
| 3,755,560 A | 8/1973 | Dickert et al. |
| 3,906,108 A | 9/1975 | Felty |
| 4,247,547 A | 1/1981 | Marks |
| 4,421,769 A | 12/1983 | Dixon et al. |
| 4,466,805 A | 8/1984 | Walters et al. |
| 4,720,353 A | 1/1988 | Bell |
| 4,826,828 A | 5/1989 | Wilmott et al. |
| 5,559,149 A | 9/1996 | Clum et al. |
| 5,656,672 A | 8/1997 | Collin et al. |
| 5,980,917 A * | 11/1999 | Kang ............... A61K 8/0295 424/401 |
| 6,113,928 A | 9/2000 | Nogueira et al. |
| 7,041,767 B2 | 5/2006 | Lange et al. |
| 7,217,777 B2 | 5/2007 | Lange et al. |
| 7,374,779 B2 * | 5/2008 | Chen .................. A61K 9/1617 424/451 |
| 7,465,439 B2 | 12/2008 | Avery et al. |
| 8,790,720 B2 | 7/2014 | Richards et al. |
| 2003/0165546 A1 * | 9/2003 | Resch ................ A61K 8/34 424/401 |
| 2003/0232091 A1 | 12/2003 | Shefer et al. |
| 2005/0137260 A1 | 6/2005 | Raschke et al. |
| 2008/0206373 A1 | 8/2008 | Millikin et al. |
| 2010/0272667 A1 | 10/2010 | Kyte, III et al. |
| 2013/0243836 A1 * | 9/2013 | Tanner ............... A61Q 19/00 424/401 |

FOREIGN PATENT DOCUMENTS

| | | |
|---|---|---|
| CN | 101756830 | 6/2010 |
| CN | 105496801 A | 4/2016 |
| DE | 19946184 A1 | 3/2001 |
| EP | 0330496 A2 | 8/1989 |
| EP | 0343444 B1 | 1/1992 |
| FR | 2835746 A1 | 8/2003 |
| KR | 20110138527 A | 12/2011 |
| WO | WO9300085 A1 | 1/1993 |
| WO | WO2004093841 A1 | 11/2004 |
| WO | WO2010134048 A2 | 11/2010 |

OTHER PUBLICATIONS chemistscorner.com "Required HLB for caprylic/capric triglyceride," printed 2018; https://chemistscorner.com/cosmeticsciencetalk/discussion/3109/required-hlb-for-caprylic-capric-triglyceride.*
RFA Vitamin Conversion Chart, copyright 2008; http://www.rfaregulatoryaffairs.com/images/pdfs/vitamin_conversion.pdf.*
International Search Report and Written Opinion of the International Searching Authority, PCT/US2017/065945, dated Apr. 24, 2018, 17 pages.

* cited by examiner

*Primary Examiner* — Trevor Love
(74) *Attorney, Agent, or Firm* — John G. Powell

(57) ABSTRACT

Personal care compositions that include a stable O/W emulsion, a stable retinoid, an oil, a fatty alcohol, and an emulsifier and methods of using such compositions to regulate a condition of mammalian keratinous tissue. By combining the oil and retinoid at a particular ratio in the personal care composition, the stability of the retinoid can be improved.

8 Claims, No Drawings

STABLE PERSONAL CARE COMPOSITIONS CONTAINING A RETINOID

FIELD

The present invention generally relates to a stable personal care composition containing a retinoid. More specifically, the present invention relates to a personal care composition in the form of an oil-in-water emulsion containing a stable retinoid.

BACKGROUND

Many personal care products currently available to consumers are directed primarily to improving the health and/or appearance of skin and/or hair. For example, there are a variety of topical skin care products available that are directed to delaying, minimizing, or even eliminating skin wrinkling and other histological changes typically associated with the aging of skin or environmental damage to human skin. For at least some people, fine lines and wrinkles in the skin are a reminder of the disappearance of youth. As a result, the elimination of wrinkles has become a booming business in youth-conscious societies. Treatments range from cosmetic creams and moisturizers to various forms of cosmetic surgery.

It is not uncommon for personal care products such as skin lotions and creams to include vitamins, vitamin derivatives, or other active ingredients for improving skin appearance. For example, vitamin A, also referred to as retinol, is known for use in topical skin care compositions to provide skin health and/or appearance benefits. Vitamin A, along with its derivatives, form a class of compounds commonly referred to as "retinoids." At one time, retinoids were primarily used for the treatment of acne. More recently, retinoids have also been used in the treatment of photo- and/or intrinsically-aged skin. While retinoids may provide desirable skin health and/or appearance benefits, some retinoids such as retinol and retinoic acid have been associated with skin irritation. As a result, retinyl esters such as retinyl acetate and retinyl palmitate, which have been shown to be milder on skin compared to retinols and retinoic acid, are sometimes included in skin care compositions. However, these milder forms of retinoids may not provide the same benefit(s) (e.g., exfoliation) or level of benefit as retinol or retinoic acid.

Retinoids can also be undesirably reactive and susceptible to degradation, leading to a shorter than desired product shelf life (e.g., product yellowing or acidification). Some known sources of degradation include oxidation, light exposure (e.g., ultraviolet radiation), and heat (e.g., temperatures of 40° C. or more). Thus, additional processing steps and/or packaging constraints may be needed to minimize degradation of the retinoid in a personal care composition. For example, careful processing in an oxygen-free environment, use of an oxygen impermeable packaging, and/or the inclusion of one or more anti-oxidants and/or chelating agents added to the composition may at least partially alleviate the amount and/or rate of retinoid degradation. However, special packaging and processing steps are not always practical or economical. And even when implemented, such steps may not be enough to suitably alleviate retinoid degradation issues.

When formulating personal care products containing retinoids, the product should be aesthetically pleasing, deliver active ingredients as intended, and exhibit suitable stability. In some instances, such retinoid containing compositions are in the form of an oil-in-water ("O/W") emulsion system, wherein the retinoid is carried primarily within the oil phase and is protected from oxidation by an oil-soluble antioxidant. See, e.g., U.S. Pat. Nos. 3,906,108; 4,466,805; and 4,247,547. When compared to water-in-oil (W/O) emulsions, O/W emulsions are sometimes thought to be less greasy feeling, more compatible with other such emulsion products, less occlusive, easier to remove from the skin, more aesthetically pleasing, and/or more economical to manufacture. However, it has been shown that retinyl esters in such compositions quickly lose their activity and either oxidize or isomerize to non-efficacious chemical forms. Thus, the amount of retinoid actually available to provide a beneficial effect is reduced, in an unacceptably short period of time, to an ineffective quantity and eventually to only trace quantities. See, WO93/00085.

To overcome the lack of retinoid stability in an O/W emulsion system, some manufacturers turned to a water-in-oil emulsion system, for example, as described in U.S. Pat. Nos. 4,826,828 and 4,720,353; European Patent Nos. EP 0,343,444 and EP 0,330,496. However, the use of W/O emulsions, with or without additional oil soluble antioxidants, still fail provide suitable retinoid stability.

Accordingly, it would be desirable to provide a stable, retinoid-containing skin care composition in the form of an oil-in-water emulsion. It would also be desirable to provide a stable, retinoid-containing skin care composition that does not irritate skin.

SUMMARY

Provided herein are personal care compositions intended for topical application to mammalian keratinous tissue. The personal care compositions include a dermatologically acceptable carrier in the form of an O/W emulsion; retinoid; an oil, wherein the weight ratio of oil to retinyl propionate is about 5:1 to about 50:1; an emulsifier, wherein the weight ratio of oil to emulsifier about 4:1 to about 50:1; and a fatty alcohol, wherein the ratio of fatty alcohol to emulsifier is about 1:1: to about 11:1. Also provided herein are methods of regulating a condition of mammalian keratinous tissue by topically applying the composition above to a target portion of mammalian keratinous tissue in need of treatment or where treatment is desired.

DETAILED DESCRIPTION

Prior to the present discovery, stabilizing a retinoid, especially a retinyl ester, in a water-in-emulsion system was problematic. Surprisingly, it has now been discovered that certain oils and/or silicone fluids (e.g., fatty acid esters and/or silicone fluid such as caprylic/capric triglyceride and cyclomethicone/dimethicone) can help stabilize retinoids in an O/W emulsion system, especially when combined with an emulsifier, fatty alcohol, and/or swellable polymer at a particular ratio. In particular, by including such fatty acids and retinoids in an O/W emulsion at a particular ratio, the stability of the retinoid can be improved.

The personal care compositions herein exhibit good stability. In order to measure the stability of a product, certain stability criteria can be established. Such criteria can be based on the percentage of retinoid (by mass) remaining in a personal care product after a given time at a given temperature. For example, if retinol was added to a product at 0.1%, and 0.087% of the retinol remained after 4 weeks storage at 40° C., then such a product is said to have retained 87% of the original retinol after 4 weeks storage at 40° C.

Stability tests, such as shelf-life tests, may also be used to evaluate stability of personal care compositions. In order to evaluate the stability of a retinoid in a given composition, the composition may be placed in a container that limits the free flow of oxygen (e.g., an aluminum tube, laminated tube, glass jar, HDPE jar, PP jar, HDPE pump) and stored for 12 weeks at a constant 40° C. The percentage loss of retinoid can be measured after an elapsed time period.

As used in the description and the appended claims, the singular forms "a," "an," and "the" are intended to include the plural forms as well, unless the context clearly indicates otherwise. All percentages disclosed herein are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. All numeric ranges are inclusive of narrower ranges and combinable; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Definitions

"Actives" means compounds that, when applied to keratinous tissue and/or a target portion of keratinous tissue, provide a benefit or improvement to the keratinous tissue. The actives herein can be skin care actives, hair care actives, or a combination thereof.

"Apply" or "application", as used in reference to a composition, means to apply or spread the compositions of the present invention onto a human skin surface such as the epidermis.

"Derivative" means a molecule similar to that of another one, but differing from it with respect to a certain functional moiety (e.g., esters, ethers, amides, amines, carboxylic acids, hydroxyls, acetyls, thiols, halogens, thiols, and/or salt derivatives of the relevant molecule).

"Dermatologically acceptable" means that the compositions or components thereof so described are suitable for use in contact with mammalian keratinous tissue without undue toxicity, incompatibility, instability, allergic response, and the like.

"Effective amount" means an amount of a compound or composition sufficient to significantly induce a positive benefit to keratinous tissue, such as a health, appearance, and/or feel benefit, including, independently or in combination, the benefits disclosed herein, but low enough to avoid serious side effects (i.e., to provide a reasonable benefit to risk ratio, within the scope of sound judgment of the skilled artisan). An effective amount of a retinoid is an amount of sufficient to regulate a desired condition of mammalian keratinous tissue when topically applied thereto in a personal care composition over the course of a treatment period.

"Hair conditioning agent" includes cationic surfactants, high melting point fatty compounds, a silicone compounds, and mixtures thereof that provide a conditioning benefit to hair. Hair care compositions that include a hair conditioning agent may be referred to as "hair conditioners." However, it is to be appreciated that shampoos may also include a hair conditioning agent.

"Keratinous tissue" refers to keratin-containing layers disposed as the outermost protective covering of mammals which includes, but is not limited to, skin, hair, nails, cuticles, etc.

"Personal care composition" means a topical composition for regulating a condition of mammalian keratinous tissue (e.g., skin, hair, finger nails). Some nonlimiting examples of personal care compositions include skin creams, lotions, and serums; shave prep compositions; body washes; deodorants and antiperspirants, shampoos; conditioners; combinations of these and the like.

"Regulating the condition of mammalian keratinous tissue," as used herein, means improving the appearance and/or feel of keratinous tissue.

"Retinoid containing personal care products" refers to any personal care product that contains a retinoid. Preferred personal care products include products used for regulating the condition of skin, even more preferably reducing the appearance of skin aging and/or reducing the appearance or occurrence of skin acne. The retinoid containing personal care products herein may also exhibit an absence of significant (e.g., consumer-unacceptable) skin irritation and good aesthetics.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

"Stable," when referring to a retinoid contained in a personal care composition, means less than 25% (e.g., less than 20%, 15%, 10%, or even less than 5%) of the retinoid present in the personal care composition degrades (i.e., chemically converted to a different compound via, for example, oxidation or some other chemical process) when the composition is subjected to environmental conditions commonly experienced by a personal care compositions of the type (e.g., 40° C. for 2 or more weeks, 1 month or more, 2 months or more, or 3 months or more). In some instances, the retinoid may be stable at 50° C. for more than 2, 4, or even 8 weeks. A suitable method of determining retinoid stability is described in the HPLC Method in more detail below.

"Topical" refers to a composition that is intended to be applied to a bodily surface such as skin or hair.

Personal Care Composition

The personal care compositions herein include a dermatologically acceptable carrier in the form of a stable oil-in-water emulsion. The stable O/W emulsion comprises a continuous aqueous phase, which typically includes water, water miscible liquids, and/or water soluble materials, and a dispersed hydrophobic phase, which typically includes lipids, oils, and/or oily materials. The O/W emulsions herein may include 1% to 50% (e.g., 1% to 30%) by volume of the dispersed hydrophobic phase and 1% to 98% (e.g., 40% to 90%) by volume of the continuous hydrophilic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73-92.

The dermatologically acceptable carrier enables other components (e.g., actives) to be delivered to the skin at an appropriate concentration. The carrier can thus act as a diluent, dispersant, solvent, or the like for particulate material, which helps ensure that it can be applied to and distributed evenly over the selected target at an appropriate concentration. The carrier may contain one or more dermatologically acceptable solid, semi-solid or liquid fillers, diluents, solvents, extenders and the like. The carrier may be solid, semi-solid, or liquid. In some instances, the carrier can be inert or it can provide benefits of its own to keratinous tissue. Concentrations of the carrier can vary with the carrier selected and the intended concentrations of the composition components.

The type of carrier utilized in the present personal care composition depends on the type of product form desired for the composition. The topical composition useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes.

The carriers herein contain a dermatologically acceptable, hydrophilic diluent. As used herein, "diluent" includes materials in which the particulate material of the composition can be dispersed, dissolved, or otherwise incorporated. Nonlimiting examples of hydrophilic diluents are water, organic hydrophilic diluents such as lower monovalent alcohols (e.g., $C_1$-$C_4$) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Water is a particularly suitable diluent. The composition preferably comprises from about 60% to about 99.99% of the hydrophilic diluent.

The present composition may be made by conventional methods of making personal care compositions comprising an O/W emulsion system, which are known to those skilled in the art.

Retinoid

The personal care compositions herein include a safe and effective amount of a retinoid. As used herein, "retinoid" includes all natural and/or synthetic analogs of Vitamin A or retinol-like compounds which possess the biological activity of Vitamin A in the skin, as well as the geometric isomers and stereoisomers of these compounds. For example, the retinoid may be a retinol ester (e.g., $C_2$-$C_{22}$ alkyl esters of retinol, including retinyl palmitate, retinyl acetate, and retinyl propionate), retinol aldehydes, retinal, beta-carotene, and/or retinoic acid (including all-trans retinoic acid and/or 13-cis-retinoic acid). A particularly suitable example of a retinoid for use in the present composition is retinyl propionate ("RP"). These compounds are well known in the art and are commercially available from a number of sources, e.g., Sigma Chemical Company (St. Louis, Mo.), Boerhinger Mannheim (Indianapolis, Ind.), BASF (Mt. Olive, N.J.), and Roche (Basel, Switzerland). Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]-nicotinate).

The retinoid may be included as a pure or substantially pure material, or as an extract obtained by suitable physical and/or chemical isolation from natural (e.g., plant) sources.

The present composition may contain 0.0001% to 2% (e.g., 0.005% to 2%, 0.01% to 1%, or even 0.01% to 0.5%) of the retinoid. For example, retinol may be present at 0.01% to 0.15%; retinol esters (e.g. retinyl propionate, retinyl acetate, retinyl palmitate) may be present at 0.01% to 2% (e.g., 0.1% to 0.5% or 0.2% to 0.4%); retinoic acids may be present at 0.01% to about 0.25%; and/or tocopheryl-retinoate, adapalene, and tazarotene may be present at 0.01% to 2%. In some instances, mixtures of more than one retinoid may be used.

The retinoid present in the personal care compositions herein is stable. In order for the personal care composition to provide the desired health or appearance benefit, it is important to provide a suitable amount of retinoid active. Thus, less than 25% (e.g., less than 20%, 15%, or even less than 10%) of the retinoid in the present compositions is lost (i.e., degraded) between the time the composition is packaged by the manufacturer and the time the package is first opened by a consumer. A suitable method for determining the amount of retinoid loss is described in more detail below.

Oil

The present composition includes 1% to 50% of an oil with a hydrophile-lipophile balance (HLB) value of between 6 and 11.5. The HLB value of the oil helps ensure that the retinoid and other oil soluble actives are fully soluble in the oil and to help maintain proper portioning of the oil droplets in the emulsion. The oil may be an emollient (i.e., a water-immiscible, oily or waxy materials used to increase the occlusive properties of skin), but need not necessarily be. It is believed, without being limited by theory, that certain oils can help stabilize a retinoid in an O/W emulsion by increasing retinoid partitioning in the oil droplets of the internal phase, thereby reducing the interaction between the retinoid and water present in the continuous phase of the emulsion. Thus, it can be important to ensure that a suitable amount of oil is present in the composition and the ratio of oil relative to other ingredients is within a particular range. If there is too much oil present in the composition then the emulsion may become unstable and/or may cause undesirable consumer performance (e.g., greasy or tacky feel and/or reduced skin penetration). On the other hand, if there is not enough oil present in the composition, then increased partitioning in the oil/water interface may lead to increased retinoid degradation and/or reduced penetration of the retinoid into keratinous tissue. In some instances, the weight ratio of oil to retinoid in the present composition is between 5:1 to 50:1 (e.g., 15:1 to 35:1 or even from 18:1 to 30:1).

Some non-limiting examples of oils that may be suitable for use in the present composition are capric/caprylic triglyceride, coconut oil, argan oil, avocado oil, jojoba oil, moringa oil, soybean oil, *Butyrospermum parkii* (shea) nut extract, *Vitis vinifera* (grape) seed oil, *Crambe abyssinica* seed oil, *Raphanus sativus* (radish) seed extract, *Argania spinose* kernel oil extract, *Limnanthes alba* (meadowfoam) seed oil, *Triticum vulgare* (wheat) germ oil, *Olea europaea* (olive) fruit oil, hydrogenate vegetable oils, shea butter ethyl esters, canola oil, c10-18 triglyceride, hydrogenate palm oil, hydrogenate coco-glyceride, *Cucurbita pepo* (pumpkin) seed oil, Sunflower seed oil, rose hip oil, safflower oil, tea tree oil, lavender oil, flaxseed oil, isoamyl cocoate, phenoxyethyl caprylate, pentaerythrityl tetraethylhexanoate, pentaerythrityl tetraisostearate, glycereth-5 lactate, c12-15 alkyl benzoate, bis-phenylpropyl dimethicone, cyclopentasiloxane, octyldecanol, hexyldecanol, heptyl undecylenate, dimyristyl tartrate, hydrogenate polydecene, propylene glycol ricinoleate, peg-7 cocoate, decyltetradecanol, isopropyl lauroyl sarcosinate, octyldodecyl myristate, diisooctyl adipate, diisostearyl malate, hydrogenate castor oil, squalane, isohexadecane, ppg-15 stearyl ether, isopropyl myristate, phenyl trimethicone, propandiol diisostearate, dimethicone, dicaprylyl ether, octyl salicylate, isopropyl isostearate, and combinations of these. Capric/caprylic triglyceride, which is available, for example, as MYRITOL 318 from BASF, may be particularly suitable for use in the present composition.

Emulsifier

The present composition includes an emulsifier to help stabilize the O/W emulsion. The emulsifier can be nonionic, anionic or cationic. Some non-limiting examples of emulsifiers are disclosed in U.S. Pat. Nos. 3,755,560 and 4,421,769 and McCutcheon's Detergents and Emulsifiers, North American Edition, pages 317-324 (1986). A particularly suitable example of an emulsifier is cetearyl glucoside/cetearyl alcohol, which is available as EMULGADE 68 from BASF. The emulsifier may be present at 1% to 10% (e.g., 2% to 5%) by weight of the composition. The amount and type of emulsifier(s) selected for use in the present compositions may vary based on the type and amount of oil(s) present. In some instances, the present composition may have a ratio of oil to emulsifier of between 4:1 and 50:1 (e.g., 5:1 to 30:1, 10:1 to 20:1 or even about 15:1).

Fatty Alcohol

The present composition also includes a fatty alcohol. The fatty alcohol may functions as an emollient, emulsifier, thickener, structurant, and/or carrying agent for oil soluble ingredients in the composition. Some non-limiting examples of fatty alcohols for use in herein are cetyl alcohol, stearyl alcohol, cetearyl alcohol (e.g, STENOL 1822 from Cognis Corporation), behenyl alcohol (e.g., LANETTE 22 from Cognis Corporation), arachidyl alcohol, lignocaryl alcohol, and combinations thereof. A particularly suitable example of a fatty alcohol for use herein is cetearyl alcohol used as an emulsifier.

It is believed, without being limited by theory, that the combination of emulsifier, fatty alcohol, and solvent creates a lamellar liquid crystal gel network in which the droplets of retinoid/oil are formed. Thus, it can be important to provide a suitable ratio of emulsifier to fatty alcohol in the present composition to produce a stronger lamellar gel-network/liquid crystal that makes less water available to react with the retinoid. Accordingly, the weight ratio of emulsifier to fatty alcohol herein is typically between 1:11 and 1:1 (e.g., between 1:10 and 3:5).

The personal care composition herein may include a water-swellable material that acts to bind the water in the composition. By binding some of the water in the personal care composition the interaction between the water and the retinoid may be reduced. Water-swellable materials for use in the present composition may be natural or synthetic (e.g., water-swellable clay and superabsorbent polymers). The water-swellable material may be present at 0.01% to 5% by weight of the composition.

In some instances, the water-swellable material is a superabsorbent polymer ("SAP") present in the aqueous phase of the composition as a multitude of particles. When swollen, the SAP may provide a light, cool, and silky feel during application of the present composition. The SAP particles may have a dry, number-average particle size of 100 μm or less (e.g., 50 μm or less), for example, 2 μm to 100 μm, with a median particle size of 25, or even in the range of 2 μm to 40 μm with a median particle size of 12. The SAP particles may have a water-absorbing capacity ranging from 20 to 2000 times their own weight (i.e., 20 g to 2000 g of water absorbed per gram of absorbent polymer), for example, 30 to 1500 times, 50 to 1000 times, or even 400 times. The water-absorbing characteristics of the SAP particles herein are defined at standard temperature and pressure conditions for distilled water. For example, the value of the water-absorbing capacity of a SAP herein can be determined by dispersing 0.5 g of polymer(s) in 150 g of distilled water, waiting 20 minutes, filtering the non-absorbed solution through a 150 μm filter for 20 minutes, and weighing the non-absorbed water to determine how much was absorbed by the polymer. %). In some instances, the viscosity of an SAP solution in 1% distilled water is in the range of 20 to 30 Pas (e.g., 22 to 29 Pas) at pH 4 and in the range of 23 to 28 Pas at pH 7.

Once hydrated, the SAP particles suitable for use in the present composition swell to form relatively soft beads that have a number average diameter of 10 μm to 150 μm (e.g., 20 μm to 130 μm, 30 μm-120 μm, 40 μm-100 μm, 50 μm-90 μm, or even about 70 μm). A suitable method of determining the number average diameter of swollen SAP particles is described in more detail below. It can be important to tailor the swollen particle size of the SAP so that the droplet and bead sizes of the aqueous phase before and after phase separation of the composition are the desired size. Suitable methods of tailoring the swollen particle size of an SAP are known in the art.

Some non-limiting examples of SAPs that may be suitable for use herein are crosslinked sodium polyacrylates such as those sold as: Octacare™ X100, X110, and RM100 by Avecia: Flocare™ GB300 and Flosorb 500 by SNF; Luquasorb™ 1003, 1010, 1100, and 1280 by BASF; Water Lock™ G400 and G430 (INCI name: Acrylamide/Sodium Acrylate Copolymer) by Grain Processing; Aqua Keep™ 10 SH NF, Aqua Keep 10 SH NFC, sodium acrylate crosspolymer-2, by Sumitomo Seika; starches grafted by an acrylic polymer (homopolymer or copolymer) and in particular by sodium polyacrylate (INCI name: Sodium Polyacrylate Starch), such as those sold as: Sanfresh™ ST-100C, ST100MC, and IM-300MC by Sanyo Chemical Industries; hydrolysed starches grafted by an acrylic polymer (homopolymer or copolymer), in particular the acryloacrylamide/sodium acrylate copolymer, (INCI name: Starch/Acrylamide/Sodium Acrylate Copolymer) such as those sold as: Water Lock™ A-240, A-180, B-204, D-223, A-100, C-200, and D-223 by Grain Processing. A particularly suitable example of an SAP is Makimousse™ 12 and Makimouse™ 25 supplied by Kobo Products, Inc.

The present composition may include a variety of optional ingredients that are known for use in personal care composition, as long as the optional ingredient(s) do not unduly alter product stability, aesthetics, or performance. The optional ingredients, when incorporated into the composition, should be suitable for contact with human keratinous tissue without undue toxicity, incompatibility, instability, allergic response, and the like within the scope of sound judgment. The CTFA Cosmetic Ingredient Handbook, Second Edition (1992) describes a wide variety of nonlimiting cosmetic and pharmaceutical ingredients. The compositions herein may from about 0.0001% to about 50%; from about 0.001% to about 20%; or, alternately, from about 0.01% to about 10%, by weight of the composition, of optional ingredients. Some non-limiting examples of optional ingredients include abrasives, absorbents, opacifying agents, colorings/colorants (e.g., pigments, dyes, and lakes), particles, essential oils, anti-caking agents, foaming agents, anti-foaming agents, oil control agents, binders, biological additives, vitamins, minerals, peptides, sugar amines, flavonoid compounds, anti-oxidants, preservatives, phytosterols, protease inhibitors, tyrosinase inhibitors, exfoliating agents, skin lightening agents, sunless tanning agents, thickeners, pH adjusters, anti-acne actives, anti-cellulite actives, anti-wrinkle actives, phytosterols and/or plant hormones, N-acyl amino acid compounds, antimicrobials, antifungals, moisturizers, emollients, humectants, lubricating agents, fragrances, anti-dandruff agents, buffering agents, bulking agents, chelating agents, biocides, denaturants, astringents, external analgesics, anti-inflammatory agents, sunscreen agents, film formers and/or polymers for aiding film-forming properties and substantivity of the composition, propellants, reducing agents, sequestrants, conditioning agents (see, e.g., U.S. Pat. Nos. 7,465,439, 7,041,767, and 7,217,777), and combinations of these. Some non-limiting examples of skin conditioning agents can be found in U.S. Pub. Nos. 2010/0272667 and 2008/0206373 and U.S. Pat. No. 8,790,720.

Method of Use

The personal care compositions herein are useful for regulating the condition of skin and/or hair while maintaining good stability. Regulating a condition of skin includes reducing the appearance of fine lines and/or wrinkles on the skin, reducing the appearance of eye bags and dark circles under the eyes, sagging skin, scars/marks, dimples, pores, stretch marks, roughness, skin surface blemishes, frown lines, expression lines, rhytides, blemishes, photodamage, crevices, and/or unevenness. Regulating the condition of skin also includes reducing the occurrence and/or appearance of acne.

The method of use may include identifying a target portion of keratinous tissue (e.g., a facial skin surface such as the forehead, perioral, chin, periorbital, nose, and/or cheek) in need of treatment and/or where treatment is desired and applying a safe and effective amount of the present composition to the target portion of tissue. The cosmetic active(s) may be incorporated into the present composition using conventional methods for combining active agents into cosmetic compositions. Without intending to be bound by theory, it is believed that application of an effective amount of the present composition to a target portion of keratinous tissue in need of treatment or where treatment is desired can provide the desired appearance benefit over the course of a treatment period.

The treatment period should be of sufficient time for the cosmetic active(s) in the present composition to provide the desired benefit to the target portion of keratinous tissue (e.g., improve appearance, increase moisturization). The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented portion of skin) while minimizing delivery to keratinous surfaces where treatment is not desired. In some instances, the composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces.

The present composition may be applied by a variety of means, including by rubbing, wiping or dabbing with hands or fingers, or by means of an implement and/or delivery enhancement device. Non-limiting examples of implements include a sponge or sponge-tipped applicator, a swab (for example, a cotton-tipped swab), a pen optionally comprising a foam or sponge applicator, a brush, a wipe, and combinations thereof. Non-limiting examples of delivery enhancement devices include magnetic, mechanical, electrical, ultrasonic and/or other energy devices. In some instances, the composition can be spread onto the skin to facilitate the separation of the aqueous phase from the oil-phase. When the aqueous and oil phases have separated, the composition may be left on the keratinous tissue. Alternatively, the composition may be allowed to remain on the skin for 5 seconds, 10 seconds, 30 seconds, or 1 minute prior to being rubbed into the keratinous tissue.

HPLC Method

This method provides a suitable means for determining the amount of RP loss in a composition.

A sufficient quantity of the test composition is placed in a controlled environment chamber/room set at 40° C. and 25% relative humidity for 1 month. After 1 month, the sample is removed from the controlled environment, equilibrated to room temperature (21° C.±2° C.) for 24 hours, and then placed in a 5° C. refrigerator until it is ready for chemical analysis. Note that retinoids are light sensitive and should not be exposed to direct light. All test compositions are mixed thoroughly before sampling.

The amount of RP loss is determined on a % w/w basis by HPLC (isocratic elution) as follows. The HPLC column(s) is conditioned in accordance with conventional practices.

Chromatographic Conditions
1. Column: C18 (5 micron), 250 mm×4.6 mm
2. Mobile Phase (Eluent): methanol/2-propanol (70/30 v/v)
3. Column temperature: approximately 25° C. (Ambient)
4. UV wavelength: 280 nm
5. Injection volume: 20 microliters
6. Flow rate: 1.0 ml/min
7. Run time: approximately 22.0 minutes
8. RP retention time: 6 minutes Mobile Phase Preparation Prepare 1 L of Mobile Phase (Eluent) by combining 700 mL of methanol with 300 mL of 2-propanol.

External Standard Preparation (Prepare Fresh on Day of Use)

In a 25 ml amber flask, dissolve 25 mg of retinyl propionate in 10 ml of Mobile Phase. Avoid exposing the RP to light. Dilute to volume with Mobile Phase. Transfer a 5.0 ml aliquot to a 50 ml amber flask and dilute to volume with mobile phase. Mix well. Filter about 1 ml of the external standard thru a suitable 0.45 micron filter (e.g., Whatman GD/X) into an amber HPLC sample vial.

HPLC Sample Preparation

Using a 1-cc tuberculin syringe, weigh and transfer 500 mg of the sample composition into a 25 ml amber volumetric flask. Add 10 mL of Mobile Phase and vortex on high for 2 minutes or until product is completely dispersed. Dilute to volume with mobile phase and mix well. Filter approximately 1 ml into an auto-sampler vial using a syringe filter (e.g., Whatman GD/X filter unit). Perform 20 injections using the condition described.

$$(A)/(B) \times (B)/(W) \times (DF) \times 100 = \text{retinyl propionate}, \% \text{ w/w}$$

Where,
$A$=peak area of retinyl propionate for the sample
$B$=peak area of retinyl propionate for the calibration
$C$=retinyl propionate standard weight in mg
$W$=sample weight, mg
$DF$=Dilution Factor (e.g., 0.1)

Emulsion Stability

This method provides a suitable method of determining whether an emulsion exhibits phases separation (i.e., a lack of stability). In this method, emulsion stability is determined by visually evaluating whether any phase separation occurs in the test compositions after one month at 40° C./25% RH. Phase separation generally manifests as a "clear" layer in the composition.

EXAMPLES

Example 1—Formulations

Tables 1A and 1B illustrate various examples of the present personal care composition. The compositions in Examples 1-16 are made as follows: add the Phase A ingredients to a suitable mixing container and heat to 75° C. while mixing. Add the Phase B ingredients to a separate container and heat to 50° C. while mixing. Add the Phase C ingredients to a separate container and mix. Add the Phase D ingredients to a separate container and mix. Mix each phase until it is homogenous. Add phase A to Phase B while mixing with a suitable mixer (e.g., propeller mixer) and then add Phase C. Continue to mix for 1 minute. Mill the Phase A/B/C mixture with a Tekmar mill TK-25 or equivalent for 2 to 3 mins at 9000-11000 RPM. Replace the mill with the propeller mixer and add Phase D to the composition while continuing to mix. Cool to 40-45° C. while continuing to mix. When the composition reaches about 42° C., replace the propeller mixer with the mill, and mill the batch for 2-3 minutes at 9,000-11,000 rpm. Transfer the batch to final container.

TABLE 1A

| | A | B | C | D | E | F | G |
|---|---|---|---|---|---|---|---|
| | | | | Weight % | | | |
| Phase A | | | | | | | |
| Myritol 318 (Capric/Caprilic Triglyceride) | 3.00 | 3.00 | 3.00 | 3.00 | 3.00 | 3.00 | 3.00 |
| Cetearyl Alcohol | 2.50 | 2.50 | 1.50 | 1.50 | 2.50 | 0.50 | 1.50 |
| Emulgade 68 (Cetearyl Glucoside and Ceteryl Alcohol) | 0.50 | 1.00 | 0.50 | 1.00 | 0.50 | 1.50 | 1.00 |
| Phase B | | | | | | | |
| Water | qs | qs | qs | qs | qs | qs | qs |
| Glycerin | 2.00 | 2.00 | 2.00 | 2.00 | 2.00 | 2.00 | 2.00 |
| Glydant Plus (DMDM Hydantoin and IPBC) | 0.15 | 0.15 | 0.15 | 0.15 | 0.15 | 0.15 | 0.15 |
| Phase C | | | | | | | |
| Retinyl Propionate | 0.40 | 0.40 | 0.40 | 0.40 | 0.40 | 0.40 | 0.40 |
| Myritol 318 (Capric/Caprylic Triglyceride) | 9.00 | 4.50 | 4.50 | 4.50 | 0.00 | 9.00 | 9.00 |
| Phase D | | | | | | | |
| Makimouse 12 (Sodium Polyacrylate Starch) | 0.40 | 0.40 | 0.40 | 0.40 | 0.40 | 0.40 | 0.40 |

TABLE 1A-continued

|  | A | B | C | D | E | F | G |
|---|---|---|---|---|---|---|---|
|  |  |  |  | Weight % |  |  |  |
| Glycerin | 1.00 | 1.00 | 1.00 | 1.00 | 1.00 | 1.00 | 1.00 |
| Total: | 100.00 | 100.00 | 100.00 | 100.00 | 100.00 | 100.00 | 100.00 |

TABLE 1B

|  | H | I | J | K | L | M | N | O |
|---|---|---|---|---|---|---|---|---|
| Phase A |  |  |  |  |  |  |  |  |
| Myritol 318 (Capric/Caprilic Triglyceride) | 3.00 | 3.00 | 3.00 | 3.00 | 3.00 | 3.00 | 3.00 | 3.00 |
| Cetearyl Alcohol | 1.50 | 0.50 | 0.50 | 0.50 | 2.50 | 2.50 | 1.50 | 0.50 |
| Emulgade 68 (Cetearyl Glucoside and Ceteryl Alcohol) | 1.00 | 1.00 | 0.50 | 1.50 | 1.50 | 1.50 | 1.50 | 0.50 |
| Phase B |  |  |  |  |  |  |  |  |
| Water | qs | qs | qs | qs | qs | qs | qs | qs |
| Glycerin | 2.00 | 2.00 | 2.00 | 2.00 | 2.00 | 2.00 | 2.00 | 2.00 |
| Glydant Plus (DMDM Hydantoin and IPBC) | 0.15 | 0.15 | 0.15 | 0.15 | 0.15 | 0.15 | 0.15 | 0.15 |
| Phase C |  |  |  |  |  |  |  |  |
| Retinyl Propionate | 0.40 | 0.40 | 0.40 | 0.40 | 0.40 | 0.40 | 0.40 | 0.40 |
| Myritol 318 (Capric/Caprylic Triglyceride) | 0.00 | 4.50 | 0.00 | 0.00 | 9.00 | 0.00 | 4.50 | 9.00 |
| Phase D |  |  |  |  |  |  |  |  |
| Makimouse 12 (Sodium Polyacrylate Starch) | 0.40 | 0.40 | 0.40 | 0.40 | 0.40 | 0.40 | 0.40 | 0.40 |
| Glycerin | 1.00 | 1.00 | 1.00 | 1.00 | 1.00 | 1.00 | 1.00 | 1.00 |
| Total: | 100.0 | 100.0 | 100.0 | 100.0 | 100.0 | 100.0 | 100.0 | 100.0 |

Example 2—Stability

This example demonstrates the improved stability of the present compositions. Examples A to O in Tables 1A and 1B were tested to measure RP degradation and emulsion stability. The temperature is selected based on the highest average temperature that a personal care composition is exposed to during typical manufacture, shipping, and/or storage conditions. The retinoid used in this example is retinyl propionate ("RP"). The results of the stability testing are summarized in Table 2.

TABLE 2

| Example | Oil/Emulsifier ratio | Oil/RP ratio | % RP Lost | Emulsion Stability |
|---|---|---|---|---|
| F | 16:1 | 30:1 | 7.5 | No separation |
| L | 16:1 | 30:1 | 7.5 | No separation |
| G | 24:1 | 30:1 | 7.69 | No separation |
| O | 48:1 | 30:1 | 9.75 | No separation |
| A | 48:1 | 30:1 | 10 | No separation |
| N | 10:1 | 18.75:1 | 10.52 | No separation |
| B | 15:1 | 18.75:1 | 14.06 | No separation |
| I | 15:1 | 18.75:1 | 14.62 | No separation |
| C | 30:1 | 18.75:1 | 15.38 | No separation |
| D | 15:1 | 18.75:1 | 15.38 | No separation |
| E | 12:1 | 7.5:1 | 16.21 | No separation |
| M | 4:1 | 7.5:1 | 18.42 | No separation |
| J | 12:1 | 7.5:1 | 20.51 | No separation |
| H | 6:1 | 7.5:1 | 21.61 | No separation |
| K | 4:1 | 7.5:1 | 22.22 | No separation |

As illustrated in Table 2, the compositions all appear to have stable emulsion systems. The data also suggest that RP stability is directly proportional to the weight ratio of oil to RP.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical personal care composition having improved stability of retinyl propionate, comprising:
    a) a dermatologically acceptable carrier in the form of an oil-in-water (O/W) emulsion;
    b) retinyl propionate;
    c) capric/caprylic triglyceride, wherein the weight ratio of capric/caprylic triglyceride to retinyl propionate is about 15:1 to about 35:1 when the composition is made;
    d) an emulsifier, wherein the weight ratio of capric/caprylic triglyceride to emulsifier is about 4:1 to about 50:1;
    e) a fatty alcohol, wherein the weight ratio of fatty alcohol to emulsifier is about 1:1: to about 11:1; and
    f) wherein less than 15% of the retinyl propionate degrades according to the HPLC Method.

2. The composition of claim 1, wherein the composition comprises about 0.0001% to about 2%, by weight of the composition, of the retinyl propionate.

3. The composition of claim 2, wherein the composition comprises about 0.01% to about 1%, by weight of the composition, of the retinyl propionate.

4. The composition of claim 1, wherein the retinyl propionate is present at about 0.1% to about 0.5%, by weight of the composition.

5. The composition of claim 1, further comprising about 0.01% to about 5%, by weight of the composition, of a water-swellable material selected from the group consisting of clays and superabsorbent polymers.

6. The composition of claim 5, wherein the water-swellable material is a superabsorbent polymer.

7. The composition of claim 6, wherein the superabsorbent polymer has a dry, number-average particle size of about 2 μm to about 100 μm.

8. The composition of claim 1, wherein the composition further comprises a skin care active selected from the group consisting of vitamins, proteins, zeolites, peptides, skin-lightening agents, sunscreen actives, terpene alcohols, desquamation actives, anti-acne actives, anti-wrinkle actives, anti-atrophy actives, anti-oxidants, flavanoids, anti-inflammatory agents, anti-cellulite agents, tanning actives, skin soothing actives, skin healing actives, conditioning agents, and combinations thereof.

* * * * *